US005600433A

United States Patent [19]
Buttry et al.

[11] Patent Number: 5,600,433
[45] Date of Patent: Feb. 4, 1997

[54] OPTICAL FIBER WAIST REFRACTOMETER

[75] Inventors: Daniel A. Buttry; Thomas C. Vogelmann; Guoying Chen, all of Laramie, Wyo.; Richard Goodwin, Bethesda, Md.

[73] Assignee: The University of Wyoming, Laramie, Wyo.

[21] Appl. No.: 334,037

[22] Filed: Nov. 2, 1994

[51] Int. Cl.⁶ .............................. G01N 21/41; G02B 6/00; G01J 1/04
[52] U.S. Cl. .................... 356/128; 356/133; 250/227.14; 385/12
[58] Field of Search .................... 356/128, 133, 356/135, 136; 250/227.14; 385/12

[56] References Cited

U.S. PATENT DOCUMENTS

| | | | |
|---|---|---|---|
| 3,282,149 | 11/1966 | Shaw et al. | 356/133 |
| 3,362,224 | 1/1968 | Melone | 356/133 |
| 3,513,319 | 5/1970 | Broerman | 250/227.25 |
| 3,999,857 | 12/1976 | David et al. | 356/133 |
| 4,287,427 | 9/1981 | Scifres | 250/577 |
| 4,827,121 | 5/1989 | Vidrine, Jr. et al. | 356/133 |
| 4,981,338 | 1/1991 | Bobb et al. | 356/128 |
| 4,988,863 | 1/1991 | Bobb et al. | 356/133 |
| 5,044,723 | 9/1991 | MacDonald | 356/128 |
| 5,047,626 | 9/1991 | Bobb et al. | 250/227.19 |
| 5,070,243 | 12/1991 | Bornstein et al. | 356/133 |
| 5,093,569 | 3/1992 | Krumboltz et al. | 250/227.16 |
| 5,115,127 | 5/1992 | Bobb et al. | 250/227.19 |
| 5,239,176 | 8/1993 | Stevenson | 356/133 |
| 5,253,037 | 10/1993 | Klainer et al. | 356/133 |
| 5,430,813 | 7/1995 | Anderson et al. | 385/12 |

FOREIGN PATENT DOCUMENTS 2103683  4/1972  France.

OTHER PUBLICATIONS

J. Opt. Soc. Am., vol. 72, pp. 198–203, "Slowly Varying Optical Fibers," by A. Ankiewicz et al., Feb. 1982.
HPLC Detection, Newer Methods, pp. 1–27, "Measurement Concepts Laser-based Detection," by Thomas Edkins, et al.
A Practical Guide to HPLC Detection, pp. 5–39, "Refractive Index Detection," by Miner Munk, 1993.
S.P.I.E., vol. 990, pp. 164–169, "An Optical Fiber Refractometer," by L. C. Bobb, et al., 1988.
Electronic Letters, vol. 20, pp. 534–535, "Novel Refractometer Using a Tapered Optical Fibre" by A. Kumar et al., Jun. 1984.
Applied Optics, vol. 28, pp. 2297, 2298–2303, "Refractive index of some mammalian tissues using a fiber optic cladding" by Frank P. Bolin, et al., Jun. 1989.

Primary Examiner—Frank Gonzalez
Assistant Examiner—Jason D. Eisenberg
Attorney, Agent, or Firm—Birch, Stewart, Kolasch & Birch, LLP

[57] ABSTRACT

The present invention relates to a refractive index detector for a dynamic liquid sample having a fiber optic filament of a predetermined diameter with an unclad sensor region, wherein the sensor region comprises a longitudinally tapered zone wherein the diameter continuously decreases from the predetermined diameter to a minimum diameter.

The invention finds use as a detector for high performance liquid chromatography and capillary zone electrophoresis.

74 Claims, 6 Drawing Sheets

FIG.4a
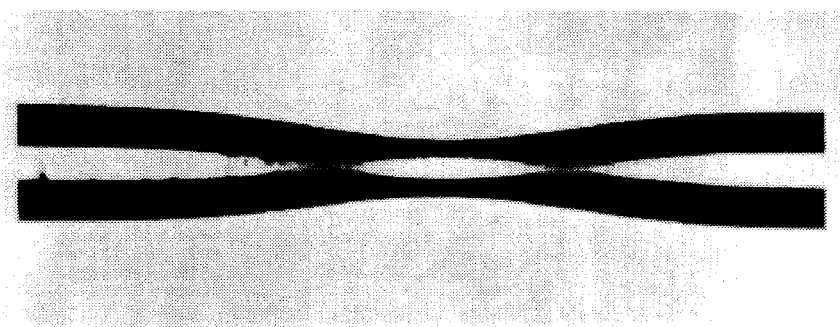
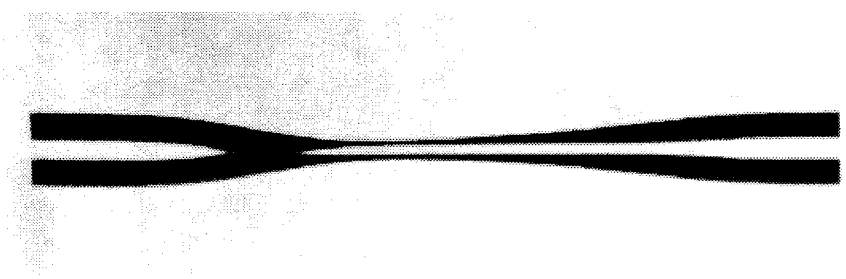
FIG.4b

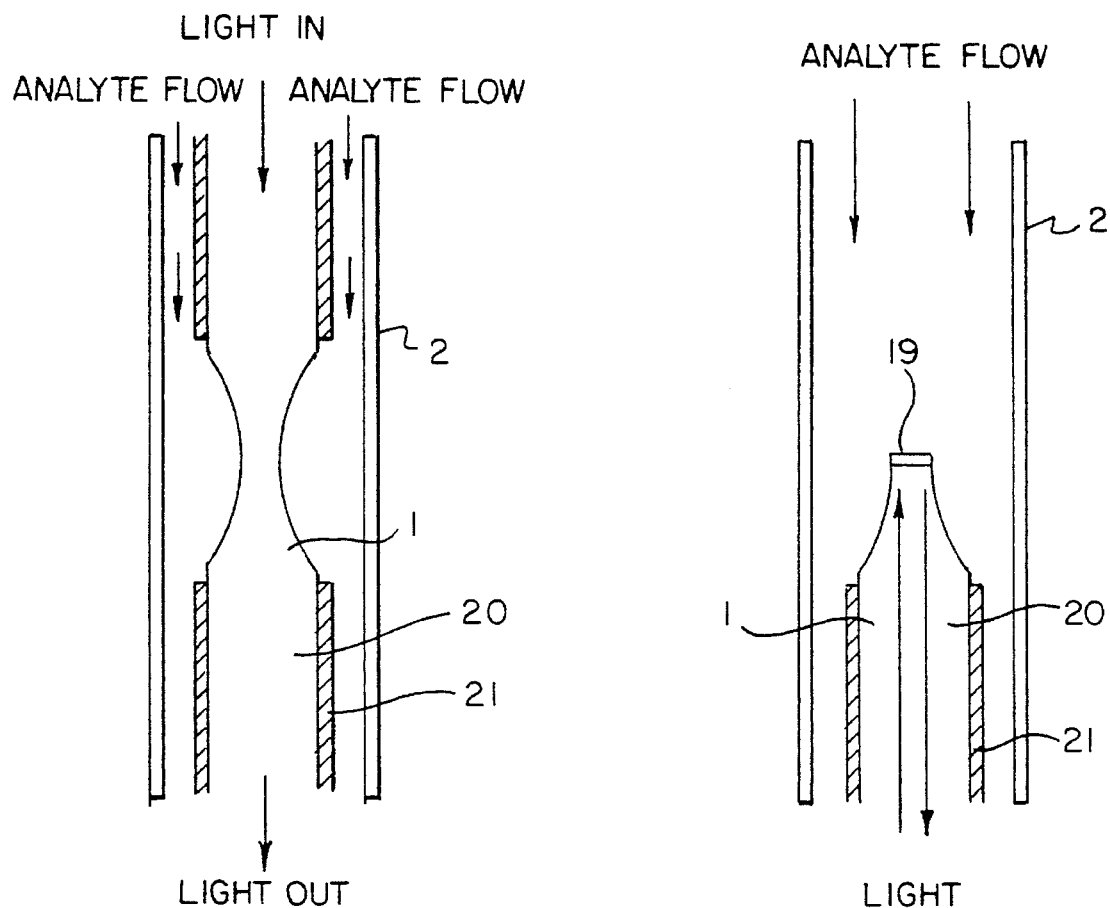
FIG. 5
FIG. 6
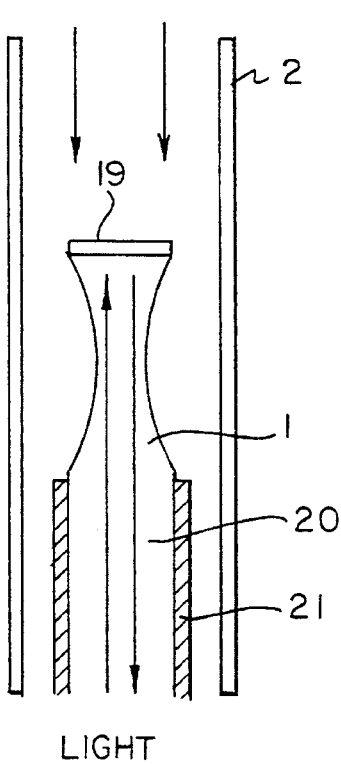
FIG. 7

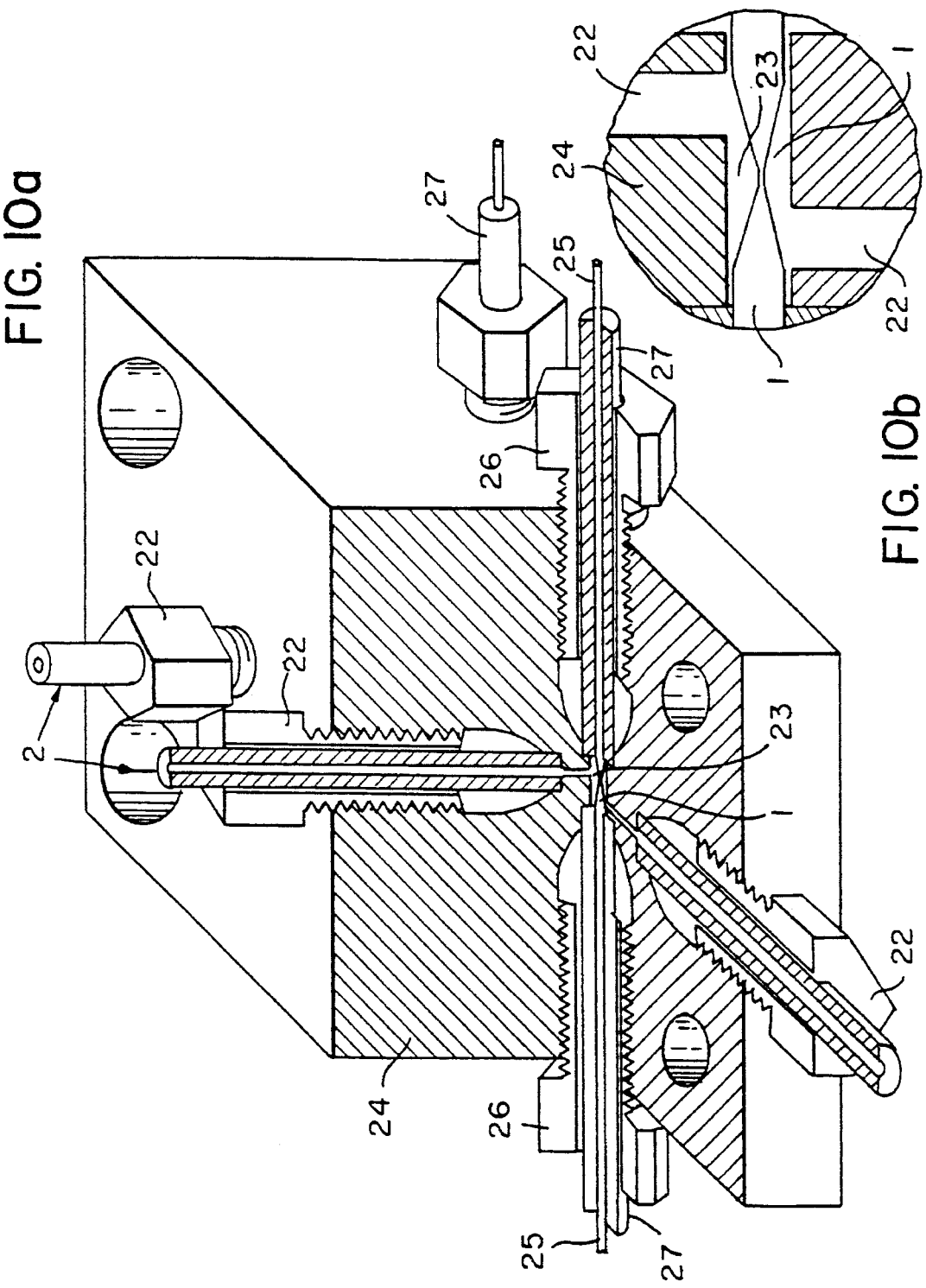

OPTICAL FIBER WAIST REFRACTOMETER

BACKGROUND OF THE INVENTION

1. Field of the Invention

The present invention relates to an optical fiber refractometer which can be used, for example, to analyze minute liquid samples.

2. Description of Related Art

In the field of analytical chemistry, it has become well-known to use the physical property of refractive index of chemicals in order to characterize various materials. For example, mixtures of chemicals may be separated by various chromatographic techniques and ultimately sent into a refractive index detector for identification and quantitation.

Recent advances in the field have enabled researchers to separate samples having smaller and smaller volumes, so as to conserve quantities of scarce or precious samples. Unfortunately, conventional refractive index detectors for chromatography require relatively large amounts of sample and are not compatible with modern capillary liquid chromatographic systems for separation of the minute samples of the present time.

It is therefore desirable to reduce the sample volume of a refractive index detector to the point that minute amounts of samples may be accurately detected, measured and quantitated in the effluent of a modern liquid chromatograph.

At the present time, no commercially available refractive index detectors exist for analysis of sample effluent from capillary zone electrophoresis (CZE) analyzers. Again, the sample volume from CZE equipment is minute and presently available refractive index detectors suffer from inadequate minimum detection levels for use with CZE.

U.S. Pat. No. 3,513,319 to Broerman discloses a refractometer having spaced light conducting rods, which may be used as a detector in a chromatographic analyzer, wherein a bundle of fiber optic tubes, having the cladding removed, is used in place of a single transparent tube of the prior art, in order to improve sensitivity for chromatographic analyzer uses.

U.S. Pat. Nos. 4,981,338 and 4,988,863 to Bobb et al. disclose an optical fiber refractometer and a method of measuring the index of refraction of a liquid by launching light into a first end of an optical fiber at a selected non-zero angle with respect to the fiber axis, wherein said optical fiber is provided with a first cylindrical region, a second tapered region, a third cylindrical region of a lesser diameter than that of the first cylindrical region and a forth tapered region.

U.S. Pat. No. 3,999,857 to David et al. discloses a refractive index detector for gradient elution chromatography with means for indicating the rate of change of refractive index, comprising a waveguide, means for contacting said waveguide with a fluid, a light source and means to transmit light into said waveguide, means for detecting light exiting from said waveguide and means to automatically change the angle of incidence of the light entering said waveguide in response to changes of refractive index of the fluid.

The disclosures of the above-cited patents are incorporated herein by reference.

SUMMARY OF TEE INVENTION

The present inventors have developed a refractive index detector for use in chemical analysis of extremely small liquid samples.

The present invention relates to a refractive index detector for a dynamic liquid sample having a fiber optic filament of a predetermined diameter with an unclad sensor region, wherein the sensor region comprises a longitudinally tapered zone wherein the diameter continuously decreases from the predetermined diameter to a minimum diameter.

Another embodiment of the present invention is a refractive index detector for a dynamic liquid sample comprising a detector block having means for liquid inlet and means for liquid outlet connecting to a sample cell disposed within the detector block, and means for inlet and outlet of a fiber optic filament of a predetermined diameter, which passes through said sample cell; a sensor mounted within said sample cell which comprises an unclad, tapered section of a fiber optic filament of a predetermined diameter and wherein the diameter of the tapered section first continuously decreases to a waist, and then continuously increases to the original, predetermined diameter; a light source which irradiates a first end of said fiber optic filament along the fiber axis; and means for monitoring variations in light intensity emitting from said sensor.

The present invention is also directed to a method of analyzing a dynamic liquid sample comprising irradiating a first end of a fiber optic filament with a light source along the fiber axis; flowing a sample-containing liquid past and in contact with a sensor which comprises said fiber optic filament having an unclad, longitudinally tapered zone wherein the diameter continuously decreases from the predetermined diameter to a minimum diameter; and measuring variations in light intensity exiting said sensor as the sample-containing liquid passes in contact with said sensor.

Another embodiment of the inventive method is a method of analyzing a dynamic liquid sample comprising irradiating a first end of a fiber optic filament of a predetermined diameter with a light source along the fiber axis; flowing a sample-containing liquid past and in contact with a sensor which comprises a fiber optic filament of a predetermined diameter having an unclad sensor region, wherein the sensor region comprises a first tapered zone wherein the diameter continuously decreases from the predetermined diameter to a minimum diameter, and a second tapered zone wherein the diameter continuously increases from the minimum diameter to the predetermined diameter, and wherein the sensor region lacks a central, cylindrical zone; and measuring the variation in light intensity exiting the sensor.

During analysis, a light beam is introduced into the optical fiber at a substantially zero-angle to the optical fiber axis, passes through the waist sensor region and the intensity of the beam exiting from the sensor region is measured and related to the refractive index of a liquid sample in contact with the sensor waist.

The refractive index detector of the present invention may be mounted within a conventional detector block for use as a chromatographic detector. Unusually, the refractive index detector of the present invention is so small that it may also be inserted into the effluent stream of a sample conditioning apparatus, such as a capillary zone electrophoresis apparatus or even a microbore capillary chromatographic column.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention.

FIGS. 4a and 4b are photomicrographs of an actual fiber optic waist sensor according to the invention.

FIG. 5 is a cross-sectional view which illustrates the first embodiment of the invention in a CZE tube.

FIGS. 6 and 7 are cross-sectional views which illustrate the second embodiment of the invention in a CZE tube.

FIG. 8b is a top view of the cubed mirrored surface of FIG. 8a.

FIG. 10a is a diagram of a detector block containing the optical fiber waist sensor of the invention, for use as a chromatographic detector.

FIG. 10b is a detailed enlargement of the detector sample cell according to the invention, when used as a chromatographic detector.

DETAILED DESCRIPTION OF THE INVENTION

The following detailed description of the invention is provided to aid those skilled in the art in practicing the present invention. Even so, the following detailed description of the invention should not be construed to unduly limit the present invention, as modifications and variations in the embodiments herein discussed may be made by those of ordinary skill in the art without departing from the spirit or scope of the present inventive discovery.

The present invention relates to a device and a method for measuring refractive indices (RI) or very small changes in refractive index of dynamic liquid samples with extremely small volumes. The measurement is based upon the loss of light intensity at a waist of an optical fiber due to changes in the critical angle condition which occur when the refractive index of the medium adjacent to the optical fiber changes.

Figure 3:
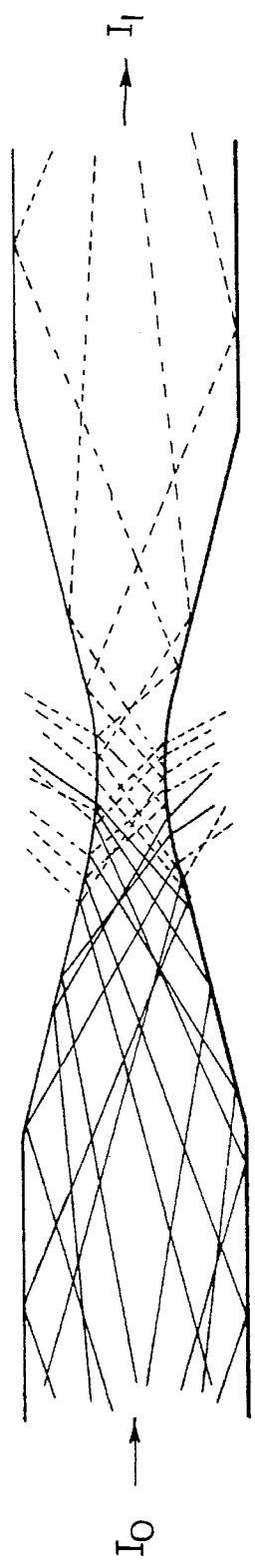
FIG. 3 is a diagram which illustrates the loss of light intensity through the fiber waist of the invention.

Specifically, when a Lambertian beam propagating along a multimode optical fiber encounters an unclad fiber waist, the critical angle condition for internal reflection (i.e. for keeping the light trapped within the fiber) is not satisfied in the region comprising the waist (see FIG. 3). Light escapes from the tapered region and the amount of light which escapes depends on the ratio of the refractive indices of the fiber material and the adjacent medium. The portion of the light which does not escape remains within the fiber core and is detected with a photodetector, such as a photodiode. Thus, the signal at the photodetector is a function of the RI of the adjacent medium, and can be used as a general RI detector.

As the loss of light is related to the critical angle condition at the fiber waist, it will be understood that controlling the taper angle of the fiber waist affects the loss of light condition. Accordingly, controlling the curvature of the waist region changes both the slope of the intensity versus RI curve and the range of RI values over which the device is sensitive.

Light loss at the fiber waist is also related to the angle of the light beams internally-reflected within the fiber optic filament. Therefore, the use of a coherent source of light, such as a laser diode, which emits light in only a few directions, results in less light loss, and therefore less sensitive detection levels, than the use of a light source which emits light at a great variety of angles, such as a light-emitting diode. Light that strikes the interface between the core material and the adjacent fluid in the waist region at "steep" reflection angles is more likely to leave the fiber at a low RI value than light that is propagated at less "steep" angles.

The optical properties of the optical fiber determine the upper limit of RI detection. The optical fiber of the present invention is a hard clad fiber which comprises a core of fused silica (quartz) and an outer polymeric cladding which is removed in the waist region. Pure quartz has an RI of 1.46, and when doped with various metals, the RI can be increased to 1.65. The RI value of the core determines the upper limit of RI detection by the present invention, because a perfect match in RI between the medium to be measured, which surrounds the fiber waist, and that of the core allows all of the light to escape from the fiber.

The lower limit of RI detection by the present invention is determined by several factors. The lower end of RI detection is determined in part by the number of modes at which one can couple the measuring light into the optical fiber, wherein a mode is related to the angle by which light is propagated through the fiber. The number of modes depends on: (a) the numerical aperture (NA) of the fiber; and (b) the light source used. For example, it is possible to couple light with more modes into a fiber which has a NA of 0.48 than one with a NA of 0.12. Similarly, it is possible to couple light with more modes by using as a light source, a light-emitting diode which emits light in many directions, rather than a laser diode which emits light at fewer directions.

Accordingly, for any given light source/fiber diameter combination, the upper and lower detection limits may be controlled by selection of the optical fiber core material (upper limit) and controlling the taper angle of the fiber waist (lower limit). The theoretical working range of the invention is from RI 1.0–1.65. However, the practical working range is narrower because it is determined by the RI values of the solvents which are in contact with the detector, which range from 1.33 (water) to 1.5 (benzene).

The present invention finds use as a general purpose RI detector for various types of analysis, including flow injection analysis (FIA), high performance liquid chromatography (HPLC), capillary zone electrophoresis (CZE) and real time in situ process monitoring. Unusually, the refractometer of the present invention is capable of measuring the RI of highly absorbing, or even opaque fluids which come into contact with the fiber waist.

Since light loss only occurs within the waist region, the overall size of the sampling "cell" necessary for use of the present invention can be extremely small. This is especially desirable for RI measurements of exotic or precious samples, as well as for the waist detector's use as a RI detector for FIA, HPLC and CZE. The minute size of the presently described RI detector enables its insertion in extremely low-dead-volume sample cells, especially advantageous for capillary HPLC, and insertion inside the capillary tubing of a CZE apparatus.

The cell volume of a typical commercial RI detector for HPLC is approximately 10 microliters. (The inventors are unaware of any commercially available RI detectors for microbore liquid chromatography or CZE). In the present invention, wherein a fiber waist is drawn from a 400 micron diameter fiber optic filament and installed in a stainless steel tube of 500 micron diameter, the resulting volume of the flowthrough cell is only 0.65 microliter. The use of optical fibers with outer diameters of 200 and 125 micron allows reduction of the sample cell volume to 35 and 5 nanoliters, respectively. In general, by appropriate changes in the fiber diameter and the inner diameter of the cylindrical region of a sample cell, it is possible to produce sample volumes ranging from 100 microliters to 5 nanoliters. In chromatography, decreases in cell volumes result in reductions in sample peak spreading and corresponding increases in sensitivity of the detector, due to increases in the signal to noise ratio of the system.

The optical fiber waists of the present invention may be produced by placing an optical fiber under tension and heating a local region so that the fiber softens and is stretched. According to this method, the optical fiber is attached to a stationary support, on one end, and to a spring on the other end. The spring is stretched such that a force of between about 5 to 40 g of tension is applied to the fiber. A small jewelers torch, with a flame temperature of about 2000° to 3000° C., is moved laterally one or more times across a region of the fiber by means of an induction motor with feedback control. The desired velocity of torch movement is from 0.2 to 0.7 cm/sec. and the distance between the torch nozzle and the optical fiber is about 0.4 to 0.8 cm. When the optical fiber softens, the maximum tension of the spring is exerted on the fiber, which stretches. However, stretching of the fiber is limited by the reduction in the displacement of the spring, which eventually returns to the "zero" position. The polymer cladding material is burned off the fiber waist by the jewelers torch.

Alternatively, for production of symmetrical tapers, the optical fiber may be attached to springs on both ends. The spring constants of these two springs must be very similar in order to produce symmetrical tapers. The other conditions are as discussed above for the case of a single spring.

The above-described method results in extremely reproducible optical fiber waist sensors having a first tapered zone, wherein the diameter continuously decreases from the predetermined maximum diameter of the fiber optic filament, to a minimum diameter, and a second tapered zone wherein the diameter continuously increases from the minimum diameter to the original maximum diameter of the fiber optic filament. The optical fiber waist sensors of the present invention lack a central, cylindrical zone. The two tapered zones may be symmetrical or asymmetrical, meaning that one may have a steeper taper angle than the other and the tapers may vary linearly or curvilinearly, having the same or different slopes, if linear, or the same or different rates of change of curvature, if curvilinear.

Alternatively, the fiber waists of the present invention may be formed by grinding or chemically etching the fiber optic filaments at the position desired for the optical sensor waist region.

A first embodiment of the invention is illustrated by FIG. 3, wherein a first end of the fiber optic filament is irradiated by a light source of an initial intensity, $I_0$, and the intensity of light exiting the fiber optic filament, $I_1$, at a second end of said fiber optic filament is monitored by a photodetector.

A second embodiment of the invention includes cleaving the fiber optic waist at approximately the minimum diameter point and disposing a reflective surface at the point of cleavage, in a plane transverse to the axis of said fiber optic filament. The reflective surface may be disposed orthogonal or oblique to the axis of the fiber optic filament, and may be flat, concave, convex or a cubed surface. Further, said reflective surface may be deposited at a point between the tapered waist sensor and the second end of said filament. In this second embodiment, the light source is positioned at a first branch of a "Y"-shaped optical coupler and incoming light, $I_0$, is reflected by said reflective surface, back through said filament to be monitored by a photodetector positioned at the second branch of said "Y"-shaped optical coupler. The bottom of the "Y" is coupled to said optical fiber filament having the tapered sensor region.

Figure 1:
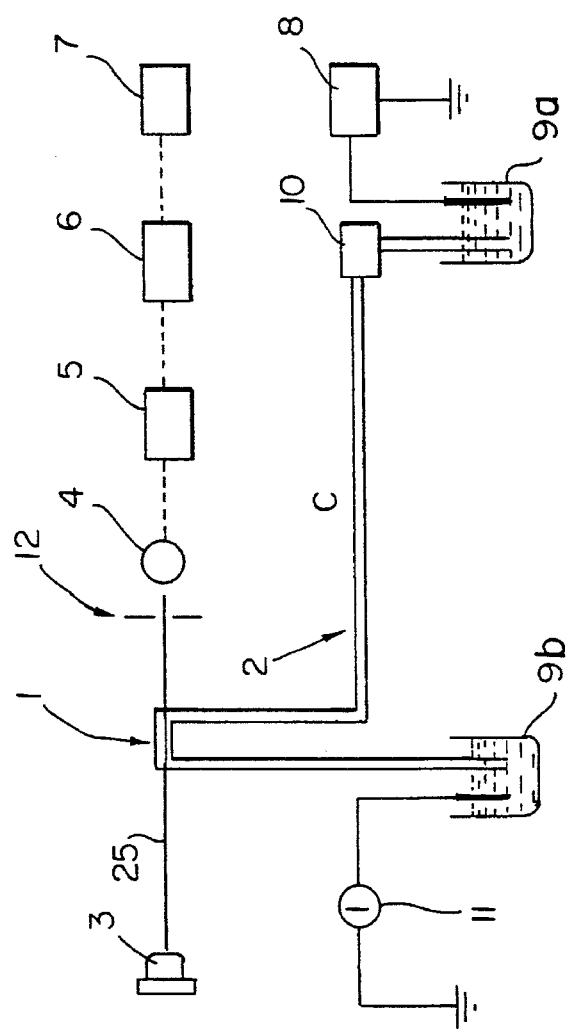
FIG. 1 is a block diagram which represents the structural configuration of a capillary zone electrophoresis (CZE) apparatus employing the refractive index detector of the invention.

FIG. 1 is a block diagram which illustrates the placement of the optical fiber waist, 1, of the present invention, within the capillary tubing, 2, of a capillary zone electrophoresis (CZE) setup, more clearly shown in FIG. 5. A high voltage power supply, 8, is provided with an electrode, which is inserted into a buffer solution, 9a. The buffer solution fills the entire capillary tube of the CZE apparatus and the high voltage circuit is completed by an electrode disposed in a second buffer vessel, 9b, and connected to an ammeter 11, which is tied to ground. Samples to be separated are injected into the system by the injector, 10, and travel through the system at differential rates determined by their individual chemical nature. As the individual sample components pass through the capillary system, each comes into contact with the optical fiber waist sensor region, 1, of the invention. A first end of the optical fiber filament, 25, containing said sensor region, 1, is irradiated by a light source, 3, along and at about a zero-angle to the axis of said optical fiber filament, 25. As the light propagates through the optical fiber filament, 25, some light is lost through the fiber waist sensor, 1. The amount of light lost is dependent upon the refractive indices (RI) of the buffer solution and the individual samples which come into contact with the fiber waist. The second end of said optical fiber filament passes through a pinhole, 12, and the light emitted from said second end of said optical fiber filament falls on a photodetector, 4. Said pinhole, 12, is disposed in the system merely to exclude room light from the photodetector, 4, and is not a required component of the optical train. The variable voltage or current signal generated by the photodetector is fed to an amplifier, 5, wherein said signal is amplified, and fed into a low-pass filter, 6. Finally, the filtered signal is recorded on a recorder, 7.

Figure 2:
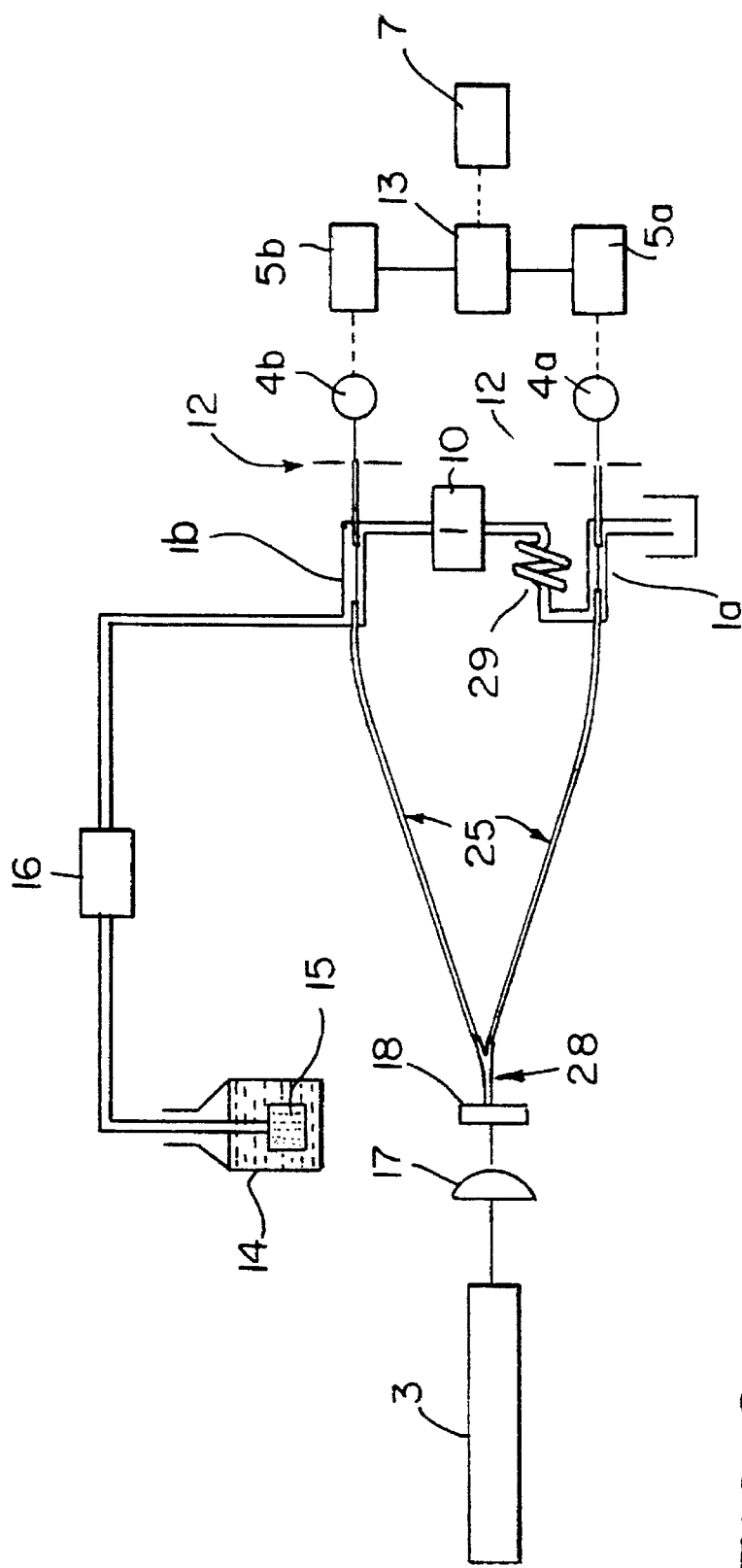
FIG. 2 is a block diagram which represents the structural configuration of a capillary liquid chromatograph employing the refractive index detector of the invention.

FIG. 2 is a block diagram of a capillary high pressure liquid chromatography setup. A solvent reservoir, 14, is filled with solvent, which passes through a solvent filter, 15, through capillary tubing to a solvent pump, 16. The solvent is pumped first into the detector block, not illustrated, and through a reference side of the refractive index detector of the invention, containing the reference fiber waist sensor, 1b. Then the solvent passes out of the detector block and through the injector, 10, wherein a sample mixture is introduced into the solvent stream. The solvent/sample mixture passes through the chromatography column, 29, and the individual components of the sample mixture are separated, according to their affinity with the stationary phase of the chromatography column, 29. The separated sample components in solvent solution, move back into the detector block and into the sample analysis side of the refractive index detector, coming into contact with the sample analysis fiber waist sensor, 1a, and ultimately flowing out of the system. A light source, 3, is provided to irradiate the sensors, 1a and 1b. Light passes from the light source, 3, through a lens, 17, through a diffuser, 18, and into the bottom of a "Y"-shaped optical coupler, 28, which splits the light beam into two equal beams, passing through the fiber optic filaments, 25, and into the detector block, to irradiate both the sample and reference sides of the detector. Light propagated past the sensor regions, 1a and 1b, passes through the remaining optical filaments, through pinholes, 12, and is emitted to fall upon the photodetectors, 4a and 4b. The variable voltage or current signals generated by photodetectors 4a and 4b are fed into amplifiers 5a and 5b, respectively. The signals are amplified and fed into the instrumentation amplifier, 13, wherein suitable processing of the amplified signals from amplifiers 5a and 5b takes place. The result of the signal processing is recorded on a recording device 7.

FIG. 3 is a diagram which illustrates the loss of light intensity through the fiber waist of the invention.

FIGS. 4a and 4b are photomicrographs of an actual fiber optic waist sensor according to the invention. FIG. 4a illustrates an optical fiber waist having symmetrical tapered zones. FIG. 4b illustrates an optical fiber waist having asymmetrical tapered zones.

FIG. 5 is a cross-sectional view of the inventive optical fiber waist sensor, 1, disposed within a capillary tube, 2, of a typical CZE apparatus. Note that the polymer cladding layer, 21, which surrounds the fiber optic core, 20, is absent in the tapered regions of the fiber waist.

FIGS. 6 and 7 illustrate the second embodiment of the present invention, wherein the tapered optical fiber sensor, 1, is provided with a reflective surface, 19, disposed on a surface in a plane transverse to the fiber optic axis.

Figure 8A:
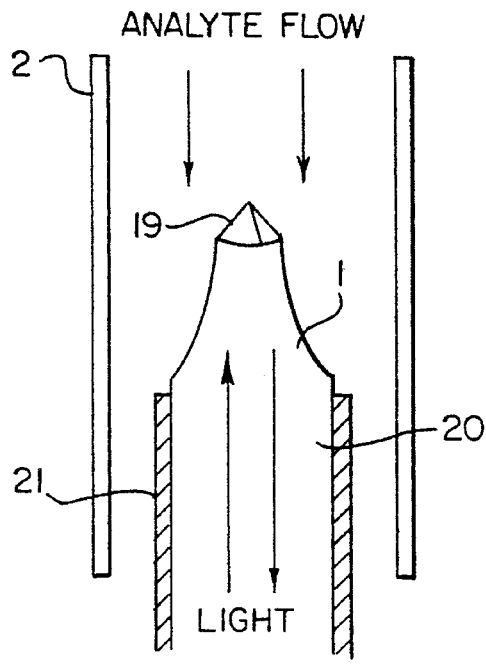
FIG. 8a is a cross-sectional view which illustrates the second embodiment of the invention in a CZE tube, wherein the mirrored surface of the sensor is cubed.
Figure 8B:
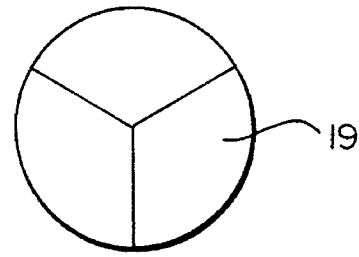

FIGS. 8a and 8b illustrate an alternative reflective surface for the sensors of the present invention, wherein the reflective surface, 19, is cubed; i.e. having the same geometry as the corner of a cube. Such a surface may be formed by grinding, polishing and coating the surface with metal.

Figure 9:
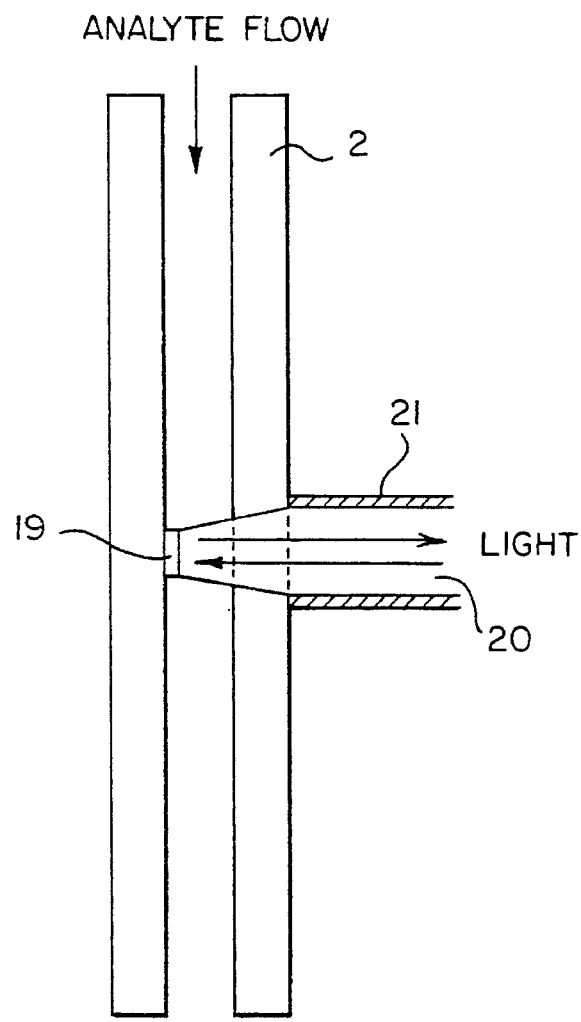
FIG. 9 is a cross-sectional view which illustrates another embodiment of the invention in a CZE tube.

FIG. 9 illustrates the second embodiment of the present invention wherein the sensor region is inserted into a hole in the side of the capillary tubing of the CZE apparatus.

FIG. 10a is a cutaway diagram of the inventive refractive index detector block for use in a chromatography system. A detector block, 24, made of a suitable, inert material, is machined to have a sample cell, 23, disposed therein. The sample cell, 23, is provided with inlet and outlet means for the sample liquid, 22, and inlet and outlet means, 26, for the fiber optic filament, 25. A PTFE sleeve, 27, surrounds the fiber optic filament, 25, at both the inlet and outlet sides, to provide mechanical support, liquid sealing capacity and additional light shielding capability. The fiber optic waist sensor, 1, is disposed within the sample cell, 23. The detector block may optionally contain a reference system, identical to the above-described sample system.

FIG. 10b is an enlargement of the sample cell, 23, of FIG. 8a, showing in greater detail the placement of the fiber optic waist sensor, 1, within the sample cell, 23, and the liquid sample inlet and outlet means, 22, disposed at either end of said sample cell, 23.

The wavelength of the light source usable with the present invention is not critical. Suitable light sources include light-emitting diodes (LED), gas lasers, laser diodes, neon lamps, xenon lamps, mercury lamps, deuterium lamps and conventional fluorescent or incandescent light sources, emitting light in the range from ultraviolet to infrared. The light sources usable with the present invention may produce a collimated or a non-collimated beam of light.

As a photodetector, any photodetector of a suitable size and sensitivity may be used. For instance, a hybrid silicon PIN type photodiode/amplifier, consisting of a silicon PIN photodiode coupled to an operational preamplifier is particularly suitable for practicing the present invention.

In general, all materials for producing the present invention should be durable and essentially chemically inert. The fused silica of the optical fiber fulfills both these requirements. The detector block may be made from materials such as stainless steel, titanium or polymers, such as polyetheretherketone (PEEK). The sleeves used to clamp the fiber optic waist into position in the detector block are suitably made from Teflon (PTFE) or the like.

When used as a chromatographic detector, the inventive refractometers may be advantageously used in a dual beam mode to (a) measure continuously the RI of the medium in the reference cell, (b) measure continuously the RI of the medium in the sample cell, and (c) continuously measure the difference in RI between the sample and reference cells. Dual beam operation results in an improvement in the signal/noise (S/N) ratio. In this regard, it is also advantageous to control the temperature of the detector block, preferably at a temperature above room temperature, through the incorporation of a heater/temperature controller system into the detector block, in order to reduce the noise level of the refractometer system. The noise level may be further reduced by conditioning the signal emitted from the amplifiers through a low-pass filter with a cutoff frequency that may vary depending upon the source of the noise.

When used as a CZE detector, the present invention provides (a) dynamic detection, (b) measurement of RI, (c) measurement of change of RI, and (d) measurement of the rate of change of RI. In this regard, the measurements of (b), (c) and (d) are simply a matter of electronic and/or mathematical manipulation. An advantage of the present invention in use as a CZE detector is that the configuration makes it easy to keep the detector response signal isolated from the CZE high voltage, since the detector element is an optical fiber, having very good electrical insulating properties. The electronic components of the RI detector of the present invention may be placed at a distance from the CZE high voltage region, thus avoiding unwanted electrical interference.

Unusually, the present refractometers may measure the RI of highly absorbing and even opaque liquids, due to the breakdown of total internal reflection in the evanescent field around the optical fiber sensor.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A refractive index detector for measuring the refractive index of a dynamic, spatially heterogeneous liquid sample, comprising:

a sensor comprising an unclad first portion of a fiber optic filament having a predetermined diameter and a longitudinally tapered unclad second portion, wherein the fiber diameter of said sensor continuously decreases curvilinearly from said predetermined diameter to a minimum diameter, said sensor lacking a cylindrical zone having said minimum diameter;

a monochromatic light source which irradiates a first end of said fiber optic filament along a fiber axis; and means for monitoring variations in light intensity emitting from said sensor.

2. The refractive index detector according to claim 1, further comprising a longitudinally tapered unclad third portion wherein the fiber diameter of said sensor continuously increases from the said minimum diameter to the predetermined diameter of said fiber optic filament.

3. The refractive index detector according to claim 1, further comprising a reflective surface disposed in a plane transverse to the axis of said filament and at said minimum diameter.

4. The refractive index detector according to claim 3, wherein said reflective surface is flat and disposed in a plane orthogonal to said filament axis.

5. The refractive index detector according to claim 3, wherein said reflective surface is flat and disposed in a plane oblique to said filament axis.

6. The refractive index detector according to claim 3, wherein said reflective surface is a concave surface.

7. The refractive index detector according to claim 3, wherein said reflective surface is a convex surface.

8. The refractive index detector according to claim 3, wherein said reflective surface is a cubed surface.

9. The refractive index detector according to claim 1, further comprising a longitudinally tapered unclad third portion, wherein the fiber diameter of said sensor continuously increases from said minimum diameter to said predetermined diameter of said fiber optic filament, having a reflective surface at an end point of said third portion, disposed in a plane transverse to the axis of said fiber optic filament.

10. The refractive index detector according to claim 9, wherein said reflective surface is flat and disposed in a plane orthogonal to said filament axis.

11. The refractive index detector according to claim 9, wherein said reflective surface is flat and disposed in a plane oblique to said filament axis.

12. The refractive index detector according to claim 9, wherein said reflective surface is a concave surface.

13. The refractive index detector according to claim 9, wherein said reflective surface is a convex surface.

14. The refractive index detector according to claim 9, wherein said reflective surface is a cubed surface.

15. The refractive index detector according to claim 1, wherein the rates of change of curvature of the curvilinearly tapered portions are the same.

16. The refractive index detector according to claim 1, wherein the rates of change of curvature of the curvilinearly tapered portions are different.

17. A refractive index detector for measuring the refractive index of a dynamic, spatially heterogeneous liquid sample comprising:

a detector block having means for liquid inlet and means for liquid outlet connecting to a sample cell disposed within said detector block, and means for inlet and outlet of a fiber optic filament of a predetermined diameter, which passes through said sample cell;

a sensor mounted within said sample cell which comprises an unclad first portion of a fiber optic filament having a predetermined diameter and a longitudinally tapered unclad second portion, wherein the fiber diameter of said sensor first continuously decreases from said predetermined diameter to a waist of a minimum diameter and then continuously increases to said original, predetermined diameter, said sensor lacking a cylindrical zone having said minimum diameter;

a monochromatic light source which irradiates a first end of said fiber optic filament along a fiber axis; and means for monitoring variations in light intensity emitting from said sensor.

18. The refractive index detector according to claim 17, wherein said light source irradiates said first end of said fiber optic filament at about a zero-angle to the fiber axis.

19. The refractive index detector according to claim 17, wherein said fiber optic filament passes axially through said sample cell.

20. The refractive index detector according to claim 17, wherein said means for monitoring variations in light intensity is a photodiode.

21. The refractive index detector according to claim 17, wherein said light source and said means for monitoring variations in light intensity are positioned outside the detector block.

22. The refractive index detector according to claim 17, having a second sensor mounted in a second sample cell which is disposed within said detector block.

23. The refractive index detector according to claim 17, wherein said sample cell is cylindrical.

24. The refractive index detector according to claim 23, wherein said means for liquid inlet and outlet are disposed at opposite ends and perpendicular to an axis of said sample cell.

25. The refractive index detector according to claim 23, wherein said sensor is mounted within said sample cell, with the axis of said sensor coinciding with an axis of said sample cell.

26. The refractive index detector according to claim 17, wherein a volume of said sample cell containing said sensor is less than 100 microliters.

27. The refractive index detector according to claim 26, wherein the volume of said sample cell is less than 0.1 microliter.

28. The refractive index detector according to claim 26, wherein the volume of said sample cell is less than 20 microliters.

29. The refractive index detector according to claim 26, wherein the volume of said sample cell is less than 1 microliter.

30. The refractive index detector according to claim 17, wherein said predetermined diameter of said fiber optic filament is less than or equal to about 400 microns.

31. The refractive index detector according to claim 30, wherein said predetermined diameter of said fiber optic filament is about 200 microns.

32. The refractive index detector according to claim 30, wherein said predetermined diameter of said fiber optic filament is about 125 microns.

33. The refractive index detector according to claim 30, wherein said predetermined diameter of said fiber optic filament is about 50 microns.

34. A refractive index detector according to claim 17, wherein the diameter of said sensor decreases and increases linearly.

35. The refractive index detector according to claim 34, wherein the linear tapered portions have the same slope.

36. The refractive index detector according to claim 34, wherein the linear tapered portions have different slopes.

37. The refractive index detector according to claim 17, wherein the diameter of said sensor decreases and increases curvilinearly.

38. The refractive index detector according to claim 37, wherein the rates of change of curvature of the curvilinearly tapered portions are the same.

39. The refractive index detector according to claim 37, wherein the rates of change of curvature of the curvilinearly tapered portions are different.

40. A method of analyzing a dynamic, spatially heterogeneous liquid sample comprising:

irradiating a first end of a fiber optic filament with a monochromatic light source along a fiber axis;

flowing a spatially heterogeneous sample-containing liquid past and in contact with a sensor which comprises an unclad first portion of said fiber optic filament having a predetermined diameter and a longitudinally tapered unclad second portion, wherein the fiber diameter of said sensor continuously decreases from said predetermined diameter to a minimum diameter, said sensor lacking a cylindrical zone having said minimum diameter; and measuring variations in light intensity exiting said sensor as said sample-containing liquid passes in contact with said sensor.

41. The method according to claim 40, wherein said light source irradiates said first end of said fiber optic filament at about a zero-angle to the fiber axis.

42. The method according to claim 40, further comprising transforming said variations in light intensity, with a photodiode, into corresponding variable electric voltage or current signals.

43. The method according to claim 40, further comprising inserting said sensor into a capillary tube in a capillary zone electrophoresis apparatus.

44. The method according to claim 40, wherein said dynamic liquid sample is flowing within a capillary tube of a capillary zone electrophoresis apparatus.

45. The method according to claim 40, wherein said sensor further comprises a reflective surface at said minimum diameter disposed in a plane transverse to the axis of said fiber optic filament.

46. The method according to claim 45, wherein said reflective surface is disposed in a plane orthogonal to the axis of said fiber optic filament.

47. The method according to claim 45, wherein said reflective surface is disposed in a plane oblique to the axis of said fiber optic filament.

48. The method according to claim 40, wherein said sensor further comprises a longitudinally tapered unclad third portion, wherein the fiber diameter continuously increases from said minimum diameter to said predetermined diameter and has a reflective surface at an end point of said third portion disposed in a plane transverse to the axis of said fiber optic filament.

49. The method according to claim 48, wherein said reflective surface is disposed in a plane orthogonal to the axis of said fiber optic filament.

50. The method according to claim 48, wherein said reflective surface is disposed in a plane oblique to the axis of said fiber optic filament.

51. The method according to claim 40, wherein said predetermined diameter of said fiber optic filament is less than or equal to about 400 microns.

52. The method according to claim 51, wherein said predetermined diameter of said fiber optic filament is about 200 microns.

53. The method according to claim 51, wherein said predetermined diameter of said fiber optic filament is about 125 microns.

54. The method according to claim 51, wherein said predetermined diameter of said fiber optic filament is about 50 microns. exiting said sensor.

55. The method according to claim 40, wherein said sensor further comprises a longitudinally tapered unclad third portion, wherein the fiber diameter continuously increases from said minimum diameter to said predetermined diameter.

56. The method according to claim 55, wherein the tapers of said tapered portions are symmetrical.

57. The method according to claim 55, wherein the tapers of said tapered portions are asymmetrical.

58. A method of analyzing a dynamic liquid sample comprising:

irradiating a first end of a fiber optic filament of a predetermined diameter with a monochromatic light source along fiber axis;

flowing a spatially heterogeneous sample-containing liquid past and in contact with a sensor which comprises an unclad first portion of said fiber optic filament having a predetermined diameter, a longitudinally tapered unclad second portion, wherein the diameter of said sensor continuously decreases from said predetermined diameter to a minimum diameter, and a longitudinally tapered unclad third portion, wherein the diameter of said sensor continuously increases from said minimum diameter to said predetermined diameter, said sensor lacking a cylindrical zone having said minimum diameter; and measuring variations in light intensity exiting said sensor.

59. The method according to claim 58, wherein said light source irradiates said first end of said fiber optic filament at about a zero-angle to the fiber axis.

60. The method according to claim 58, wherein said dynamic liquid sample is an effluent stream from a capillary liquid chromatography column.

61. The method according to claim 58, further comprising transforming said variations in light intensity, with a photodiode, into corresponding variable electric voltage or current signals.

62. The method according to claim 61, wherein said photodiode is positioned at a second end of said fiber optic filament.

63. The method according to claim 58, wherein said sensor is coaxially mounted within a cylindrical sample disposed within a detector block having means for liquid inlet and means for liquid outlet connecting to said sample cell, and means for inlet and outlet of said fiber optic filament.

64. The method according to claim 63, wherein a volume of said sample cell containing said sensor is less than 100 microliters.

65. The method according to claim 64, wherein the volume of said sample cell is less than 0.1 microliter.

66. The method according to claim 65, wherein the volume of said sample cell is less than 20 microliters.

67. The method according to claim 64, wherein the volume of said sample cell is less than 1 microliter.

68. The method according to claim 58, wherein said predetermined diameter of said fiber optic filament is less than or equal to about 400 microns.

69. The method according to claim 68, wherein said predetermined diameter of said fiber optic filament is about 200 microns.

70. The method according to claim 68, wherein said predetermined diameter of said fiber optic filament is about 125 microns.

71. The method according to claim 68, wherein said predetermined diameter of said fiber optic filament is about 50 microns.

72. The method according to claim 58, wherein said dynamic liquid sample is flowing within a capillary tube in a capillary zone electrophoresis apparatus.

73. The method according to claim 72, wherein said fiber optic filament is disposed axially within said capillary tube.

74. The method according to claim 72, wherein said fiber optic filament is disposed radially through said capillary tube.

* * * * *